United States Patent [19]

Hees et al.

[11] Patent Number: 5,446,210

[45] Date of Patent: Aug. 29, 1995

[54] PROCESS FOR THE PRODUCTION OF POLYOL ETHERS

[75] Inventors: Udo Hees, Mayen; Georg Assman, Neuss; Fritz Schuster, Duesseldorf, all of Germany

[73] Assignee: Henkel Kommanditgesellschaft auf Aktien, Duesseldorf, Germany

[21] Appl. No.: 185,903

[22] PCT Filed: Jul. 13, 1992

[86] PCT No.: PCT/EP92/01587

§ 371 Date: Jan. 21, 1994

§ 102(e) Date: Jan. 21, 1994

[87] PCT Pub. No.: WO93/02033

PCT Pub. Date: Feb. 4, 1993

[30] Foreign Application Priority Data

Jul. 20, 1991 [DE] Germany ............... 41 24 199.1

[51] Int. Cl.6 .................... C06C 41/00; C06C 43/00
[52] U.S. Cl. .................... 568/678; 568/671; 568/691; 568/698; 568/650; 568/680
[58] Field of Search ............. 568/671, 691, 678, 680

[56] References Cited

U.S. PATENT DOCUMENTS

| | | | |
|---|---|---|---|
| 2,932,670 | 4/1960 | Blake | 260/615 |
| 3,350,460 | 10/1967 | Lamberti | 260/609 |
| 4,088,700 | 5/1978 | Watts | 260/611 R |
| 4,479,017 | 10/1984 | Ayusawa et al. | 568/671 |
| 4,484,009 | 11/1984 | Ghenassia et al. | 568/678 |

FOREIGN PATENT DOCUMENTS

| | | | |
|---|---|---|---|
| 0092463 | 10/1983 | European Pat. Off. | |
| 1234199 | 2/1967 | Germany . | |
| 3224033 | 1/1983 | Germany . | |
| 1020500 | 2/1966 | United Kingdom | 568/671 |

OTHER PUBLICATIONS

Verzele et al, J Chem Soc (1963) pp. 5598–5600.

*Primary Examiner*—Johann Richter
*Attorney, Agent, or Firm*—Ernest G. Szoke; Wayne C. Jaeschke; Henry E. Millson, Jr.

[57] ABSTRACT

A process for the production of polyol ethers comprising the steps of

A) reacting a mixture of at least one polyol and at least one carbonyl compound of the formula $$R^1\text{—CO—}R^2 \qquad (I)$$

in which $R^1$ and $R^2$ independently of one another represent hydrogen or aliphatic hydrocarbon radicals containing 1 to 22 carbon atoms and 0, 1, 2, or 3 double bonds, with hydrogen at an elevated temperature in the presence of a hydrogenation catalyst which is insoluble in the reaction mixture; and B) removing the polyol ether-containing reaction product from the catalyst.

20 Claims, No Drawings

PROCESS FOR THE PRODUCTION OF POLYOL ETHERS

This application is 371 of PCT/EP92/01587 filed Jul. 13, 1992.

BACKGROUND OF THE INVENTION

1. Field of the Invention

This invention relates to a process for the production of polyol ethers by catalytic reaction of mixtures of polyols and carbonyl compounds with hydrogen at elevated temperatures and under elevated pressure.

2. Statement of Related Art

Ethers of polyols, for example glycerol ethers, are surface-active substances which have excellent detergent properties and which may be used, for example, as wetting agents (U.S. Pat. No. 2,932,670), emulsifiers (DE 11 00 035 A1)] or lime soap dispersants (U.S. Pat. No. 3,350,460).

Polyol ethers are generally produced by WILLIAMSON'S ether synthesis. In this process, polyols, for example glycerol, are reacted with alkyl halides in the presence of strong bases. According to DE-PS 615 171, alkali metal salts of alkyl sulfates may be used instead of the alkyl halides.

However, the known processes mentioned above all have the disadvantage that the production of the polyol ethers is accompanied by the accumulation of salts, for example potassium chloride or sodium sulfate, which cannot remain in the product, but instead have to be removed—in some cases with considerable effort.

Another serious disadvantage is that these salts are by no means pure, but instead are contaminated with significant quantities of product. Accordingly, the disposal of these waste materials is extremely expensive and adversely affects the profitability of the process.

Accordingly, the problem addressed by the present invention was to provide a process for the production of polyol ethers which would be free from the disadvantages mentioned above.

DESCRIPTION OF THE INVENTION

The present invention relates to a process for the production of polyol ethers which is characterized in that mixtures containing a) polyols and
b) carbonyl compounds corresponding to formula (I):

$$R^1-CO-R^2 \qquad (I)$$

in which $R^1$ and $R^2$ independently of one another represent hydrogen or aliphatic hydrocarbon radicals containing 1 to 22 carbon atoms and 0, 1, 2 or 3 double bonds, are reacted with hydrogen at elevated temperatures and under elevated pressure in the presence of a catalyst which is insoluble in the reaction mixture.

It has surprisingly been found that polyol ethers can be produced without the formation of salts as secondary products providing the polyols are reacted with aldehydes or ketones and the acetals or ketals intermediately formed are simultaneously subjected, i.e. without isolation, to catalytic hydrogenation.

Polyols are compounds which contain at least two hydroxy groups. Typical examples are ethylene glycol, diethylene glycol, triethylene glycol, polyethylene glycols having an average molecular weight of 300 to 1500, propylene glycol, polypropylene glycols having an average molecular weight of 300 to 1500, propane-1,2diol, propane-1,3-diol, butane-1,2-diol, butane-1,4-diol, average molecular weight of 300 to 1500, propane-1,2diol, propane-1,3-diol, butane-1,2-diol, butane-1,4-diol, glycerol, monoesters of glycerol with $C_{6-22}$ fatty acids, diglycerol, oligoglycerols with an average degree of condensation of 3 to 10, trimethylol propane or pentaerythritol. It is particularly preferred to use glycerol.

The carbonyl compounds corresponding to formula (I) are known aldehydes and ketones which may be prepared by methods known per se. Carbonyl compounds corresponding to formula (I), in which $R^1$ and $R^2$ independently of one another represent $C_{1-18}$ alkyl groups, are preferably used.

Typical aldehydes are, for example, formaldehyde, acetaldehyde, acrolein, propionaldehyde, butyraldehyde, croton aldehyde, caproic aldehyde, caprylic aldehyde, capric aldehyde, lauryl aldehyde, myristyl aldehyde, cetyl aldehyde, stearyl aldehyde, oleyl aldehyde, elaidyl aldehyde, linolyl aldehyde, linolenyl aldehyde, behenyl aldehyde or erucyl aldehyde.

Typical ketones are, for example, acetone and the various position isomers of butanone, pentanone, hexanone and octanone and also the fatty ketones obtained by pyrolysis of the alkaline earth metal salts of $C_{12-22}$ fatty acids. It is particularly preferred to use acetone.

The polyols and the carbonyl compounds may be used in a molar ratio of 5:1 to 1:5 and preferably in a molar ratio of 1:1 to 1:4.

The hydrogenation may be carried out heterogeneously, i.e. in the presence of a catalyst which is not soluble in the reaction mixture and which may therefore be separated from the product with minimal effort after the reaction and recovered. A typical example of this is the use of transition metals such as, for example, nickel, cobalt, platinum, rhodium, ruthenium or, in particular, palladium. It is advisable to use the catalysts in finely divided form, for example as platinum sponge or palladium black or even in the form of gauzes. To carry out the process according to the invention on an industrial scale, it has proved to be optimal to fix fine-particle metal to an inorganic support, for example silicon dioxide, aluminium oxide or, in particular, active carbon. It is preferred to use palladium on active carbon, the Pd content of the catalyst being from 1 to 15% by weight and preferably from 5 to 15% by weight, based on the catalyst (metal+support). If the reaction is carried out continuously, it is advisable to use a fixed bed in which the catalyst is arranged, for example in the form of pellets.

In the reaction with hydrogen, the catalyst may be used in a quantity of 1 to 15% by weight and is preferably used in a quantity of 5 to 10% by weight, based on the starting materials.

The reaction may be carried out discontinuously or continuously. For example, the starting materials—polyol and carbonyl compound—may be introduced into a pressure vessel, for example a steel autoclave, and, after addition of the catalyst, the reaction mixture is exposed to hydrogen. Elevated temperatures and excess pressure are necessary for the acetalization or ketalization of the polyols and the simultaneous hydrogenation of the acetals or ketals formed as intermediate products. The reaction may be carried out at temperatures of 150° to 250° C. and under pressures of 50 to 150 bar. To obtain a high yield of monoethers and bisethers, it has proved to be optimal to select a temperature range of 175° to 200° C. and a pressure range of 75 to 125 bar.

In one preferred embodiment of the process according to the invention, the reaction may be carried out continuously, for example using a fixed-bed reactor. In this case, it has proved to be of particular advantage to carry out the reaction with a liquid hourly space velocity LHSV (corresponding to the throughput per reactor volume and unit of time) of 0.05 to 0.7 and preferably 0.1 to 0.3 h$^{-1}$.

The various position-isomeric polyol monoethers and bisethers may be obtained in yields of 35 to 50% of the theoretical by the process according to the invention. The secondary products are, above all, acetals or ketals, acetal ethers or ketal ethers and the hydrogenation products of the carbonyl compounds used. If desired, the polyol ethers may be enriched by removing the secondary products and unreacted polyol by distillation and returning them to the reaction. This affords the possibility of recycling which is particularly advantageous in regard to high yields of polyol ethers.

Industrial Applications

The polyol ethers obtainable by the process according to the invention have surface-active and solubilizing properties and are suitable for the production of solubilizers, emulsifiers, lime soap dispersants, wetting agents and detergency boosters, in which they may be present in quantities of 1 to 50% by weight and preferably 10 to 25% by weight, based on the particular preparation.

The following Examples are intended to illustrate the invention without limiting it in any way.

EXAMPLES

Example 1

Discontinuous hydrogenation.

A mixture of 46 g (0.5 mole) of glycerol and 58 g (1.0 mole) of acetone is introduced into a 250 ml steel autoclave, followed by the introduction of 10 g of hydrogenation catalyst (5% by weight of palladium on active carbon)—corresponding to around 10% by weight, based on the starting materials. The autoclave was closed and hydrogen was admitted at a temperature of 175° C. until a pressure of 100 bar had been established. After termination of the reaction, the autoclave was cooled and vented and the catalyst was filtered off from the liquid phase. The reaction product had the following composition:

| | |
|---|---|
| 1- or 2-glycerol monoisopropyl ether (ME) | 36% by weight |
| 1,2- or 1,3-glycerol-bis-isopropyl ether (BE) | 10% by weight |
| Glycerol isopropyl ketal (K) | — |
| Glycerol monoisopropyl ether ketal (EK) | 1% by weight |
| Glycerol (G) | 13% by weight |
| Isopropyl alcohol (iPA) | 40% by weight |

Example 2

65 g (0.7 mole) of glycerol, 40 g (0.91 mole) of acetaldehyde and 10 g of palladium on active carbon (Pd content 5% by weight, based on the catalyst) were reacted as in Example 1. The reaction was carried out over a period of 6 h at a temperature of 175° C. and under a hydrogen pressure of 100 bar. After the ethanol formed had been distilled off, a product having the following

| | |
|---|---|
| 1- or 2-glycerol monoethyl ether | 39% by weight |
| 1,2- or 1,3-glycerol bis-ethyl ether | 8% by weight |
| Glycerol | 53% by weight | composition was obtained:

Examples 3 to 5

Continuous hydrogenation.

In a fixed-bed hydrogenation reactor (capacity 1000 cm$^3$), a mixture of acetone and glycerol in a molar ratio of 2.5:1 was continuously hydrogenated on a pelleted palladium/active carbon catalyst (5% by weight Pd, based on the catalyst) at a temperature of 200° C. and under a pressure of 100 bar. The LHSV was 0.18 to 0.7 h$^{-1}$. The composition of the reaction products is shown in Table 1. No reduction in activity and no significant change in the composition of the products were observed over a period of 14 d.

TABLE 1

| | Continuous hydrogenation of acetone/glycerol Percentages in % by weight | | | | | | |
|---|---|---|---|---|---|---|---|
| Ex. | LHSV h$^{-1}$ | ME % | BE % | K % | EK % | G % | iPA % |
| 3 | 0.18 | 41 | 6 | 10 | 7 | 31 | 5 |
| 4 | 0.30 | 39 | 6 | 7 | 5 | 37 | 6 |
| 5 | 0.70 | 29 | 5 | 4 | 3 | 53 | 6 |

We claim:

1. A process for the production of polyol ethers comprising the steps of
   A) reacting a mixture of at least one polyol and at least one carbonyl compound of the formula $$R^1-CO-R^2 \qquad (I)$$

in which $R^1$ and $R^2$ independently of one another represent hydrogen or aliphatic hydrocarbon radicals containing 1 to 22 carbon atoms and 0, 1, 2 or 3 double bonds, with hydrogen at an elevated temperature in the presence of a catalyst consisting of a hydrogenation catalyst which is insoluble in the reaction mixture; and
   B) separating the polyol ether-containing reaction product from the catalyst.

2. The process of claim 1 wherein the molar ratio of polyol to carbonyl compound in step A) is from 5:1 to 1:5.

3. The process of claim 2 wherein said ratio is from 1:1 to 1:4.

4. The process of claim 1 wherein in step A) the at least one polyol is glycerol.

5. The process of claim 1 wherein in step A) in the at least one carbonyl compound $R^1$ and $R^2$ independently of one another represent $C_{1-18}$ alkyl groups.

6. The process of claim 5 wherein the at least one carbonyl compound is acetone.

7. The process of claim 1 wherein in step A the hydrogenation catalyst is present in from 1 to 15% by weight, based on the weight of said mixture.

8. The process of claim 7 wherein from 5 to 10% by weight of hydrogenation catalyst is present.

9. The process of claim 7 wherein the hydrogenation catalyst consists is palladium, optionally present on an inorganic support.

10. The process of claim 9 wherein from 5 to 15% by weight of palladium is present.

11. The process of claim 1 wherein step A) is carried out at a temperature in the range of from 150° to 250° C.

12. The process of claim 11 wherein said temperature is in the range from 175° to 200° C.

13. The process of claim 11 wherein step A) is carried out under a hydrogen pressure in the range of from 50 to 150 bar.

14. The process of claim 12 wherein step A) is carried out under a hydrogen pressure of from 75 to 125 bar.

15. The process of claim 1 wherein the process is carried out continuously at an LHSV of 0.05 to 0.7 h$^{-1}$.

16. The process of claim 15 wherein said LHSV is from 0.1 to 0.3 h$^{-1}$.

17. The process of claim 1 wherein in step A) the molar ratio of polyol to carbonyl compound is from 5:1 to 1:5; the hydrogenation catalyst is present in from 1 to 15% by weight, based on the weight of said mixture; and step A) is carried out at a temperature from 150° to 250° C. and a hydrogen pressure in the range of from 50 to 150 bar.

18. The process of claim 17 wherein the molar ratio of polyol to carbonyl compound is from 1:1 to 1:4; the hydrogenation catalyst is present in from 5 to 15% by weight; said temperature is in the range of from 175° to 200° C. and said hydrogen pressure is from 75 to 125 bar.

19. The process of claim 17 wherein in step A) the at least one polyol is glycerol; in the at least one carbonyl compound $R^1$ and $R^2$ independently of one another represent $C_{1-18}$ alkyl groups; and the hydrogenation catalyst consists of palladium, optionally on an inorganic support, present in from 5 to 15% by weight, based on the weight of said mixture.

20. The process of claim 19 wherein the at least one carbonyl compound is acetone.

* * * * *